United States Patent [19]

Yoshimoto et al.

[11] 4,308,051
[45] Dec. 29, 1981

[54] TETRAHYDROFURAN DERIVATIVES

[75] Inventors: Takeo Yoshimoto, Yokohama; Teruhiko Toyama, Chigasaki; Keiichi Igarashi, Musashino; Masaaki Ura; Yuji Enomoto, both of Yokohama; Yasunobu Funakoshi; Yoshikata Hojo, both of Chigasaki, all of Japan

[73] Assignee: Mitsui Toatsu Chemicals, Inc., Tokyo, Japan

[21] Appl. No.: 216,609

[22] Filed: Dec. 15, 1980

[30] Foreign Application Priority Data

Dec. 17, 1979 [JP] Japan .................. 54-162711

[51] Int. Cl.³ ............................................ A01N 43/08
[52] U.S. Cl. ...................................... 71/88; 260/347.8
[58] Field of Search ........... C07D/307/20; 260/347.8; 71/88

[56] References Cited

U.S. PATENT DOCUMENTS

| | | | |
|---|---|---|---|
| 3,231,358 | 1/1966 | Wilson et al. | 71/2.3 |
| 3,776,961 | 12/1973 | Theissen | 260/613 R |
| 3,798,276 | 3/1974 | Bayer et al. | 260/612 R |
| 3,849,503 | 11/1974 | Shigehara et al. | 260/613 R |
| 3,888,932 | 6/1975 | Bayer et al. | 260/612 R |
| 3,928,416 | 12/1975 | Bayer et al. | 260/471 R |
| 3,969,102 | 7/1976 | Yoshimoto et al. | 260/613 R |
| 4,039,588 | 8/1977 | Wilson et al. | 260/613 R |
| 4,062,896 | 12/1977 | Yoshimoto et al. | 260/613 R |
| 4,093,446 | 6/1978 | Bayer et al. | 260/613 R |
| 4,100,296 | 7/1978 | Farooq et al. | 424/278 |
| 4,264,777 | 4/1981 | Yoshimoto et al. | 568/568 |

FOREIGN PATENT DOCUMENTS 45-28198 9/1970 Japan .
49-236 1/1974 Japan .
50-37740 4/1975 Japan .

*Primary Examiner*—Richard Raymond
*Attorney, Agent, or Firm*—Fisher, Christen & Sabol

[57] ABSTRACT

A tetrahydrofuran derivative represented by the general formula

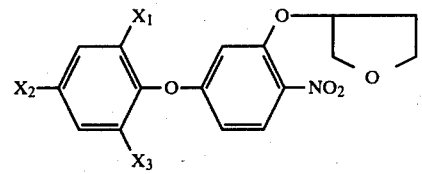

wherein $X_1$ and $X_3$ represent a hydrogen or halogen atom, and $X_2$ represents a halogen atom or a trifluoromethyl group. The compounds have excellent herbicidal activity and can be prepared by reacting a compound of the formula

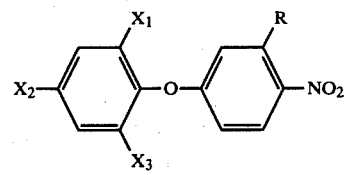

wherein R represents a nitro group or a group of the formula

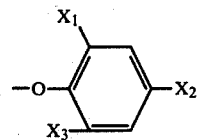

in which $X_1$, $X_2$ and $X_3$ are as defined above, with 3-hydroxytetrahydrofuran in the presence of an alkali.

8 Claims, No Drawings

TETRAHYDROFURAN DERIVATIVES

This invention relates to a tetrahydrofuran derivative represented by the general formula

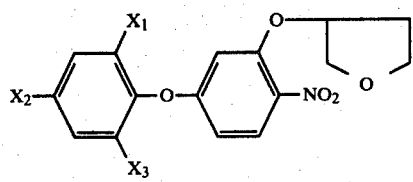

wherein $X_1$ and $X_3$ represent a hydrogen or halogen atom, and $X_2$ represents a halogen atom or a trifluoromethyl group, a process for its production, and a herbicide containing the compound of general formula (I) as an active ingredient.

We have synthesized various novel tetrahydrofuran derivatives and extensively investigated their activities as agricultural and horticultural chemicals. Consequently, we have found that the compounds of general formula (I) have excellent herbicidal activity.

The compounds of general formula (I) are produced by reacting a compound of general formula

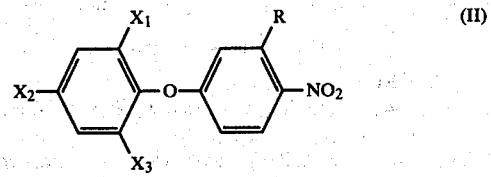

wherein R represents a nitro group or a group of the formula

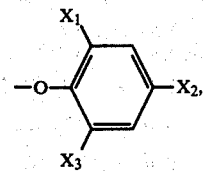

and $X_1$, $X_2$ and $X_3$ are the same as $X_1$, $X_2$ and $X_3$ in general formula (I), with 3-hydroxytetrahydrofuran in a suitable solvent in the presence of an alkali. The reaction temperature is from room temperature to 150° C., preferably from 40° C. to 80° C. The reaction time varies depending upon the solvent and the reaction temperature used. Generally, it is from 30 minutes to 5 hours, preferably from 1 hour to 2 hours. The alkali used in the reaction includes, for example, potassium hydroxide, sodium hydroxide and calcium hydroxide. Examples of suitable solvents are toluene, dioxane, ketones and dimethyl formamide. The solvent may contain some amount of water. After the reaction, the desired compound is obtained from the reaction mixture in a customary manner.

The following Synthesis Examples illustrate the production of the compound of formula (I) in detail. The compound numbers shown in these examples correspond with those given in Table 1.

SYNTHESIS EXAMPLE 1

3-[2-Nitro-5-(2-chloro-4-trifluoromethyl-phenoxy)-phenoxy]-tetrahydrofuran [compound No. (4)]:

2.7 g (0.03 mole) of 3-hydroxytetrahydrofuran was dissolved in 50 ml of dioxane, and an aqueous solution consisting of 1.7 g (0.03 mole) of potassium hydroxide and 5 ml of water was added, and the mixture was stirred at room temperature for 30 minutes. Then, a solution of 5 g (0.015 mole) of 2-chloro-4-trifluoromethyl-3',4'-dinitrodiphenyl ether in 20 ml of dioxane was added to the mixture, and the mixture was stirred at 60° to 70° C. for 2 hours. The reaction mixture was allowed to cool, and poured into 200 ml of cold water. The oily material precipitated was extracted with 200 ml of benzene with shaking. The extract was fully washed with water, and dried over anhydrous sodium sulfate. The benzene was distilled off under reduced pressure to afford 6 g (99.0%) of a pale yellow oily product. The product was chromatographed on a silica gel column using chloroform as an eluent to afford 4 g (65.6%) of the title compound.

SYNTHESIS EXAMPLE 2

3-[2-nitro-5-(2,4-dichloro-6-fluorophenoxy)-phenoxy]-tetrahydrofuran [compound No. (2)]:

3.9 g (0.045 mole) of 3-hydroxytetrahydrofuran, 2.5 g (0.045 mole) of potassium hydroxide and 100 ml of dioxane were mixed with stirring. To the resulting solution was added at room temperature, a solution of 7.2 g (0.015 mole) of 2,4-bis(2,4-dichloro-6-fluorophenoxy)-nitrobenzene in 20 ml of dioxane. Then, the mixture was stirred for 2 hours while maintaining at 60° to 70° C. to perform ether exchange reaction. The reaction mixture was allowed to cool, and poured into 300 ml of cold water. It was extracted with 200 ml of benzene with shaking. The benzene layer was fully washed with water and dried over anhydrous sodium sulfate. The benzene was distilled off under reduced pressure to afford 5.5 g (94.7%) of a pale yellow oily product. The oily product was chromatographed on a silica gel column using chloroform as an eluent to afford 4 g (68.9%) of the title compound.

Other compounds within the scope of this invention can be synthesized in accordance with Synthesis Example 1 or 2. Table 1 below summarizes the results of analysis of typical compounds (I) of this invention.

TABLE 1

| Compound No. | Substituents in formula (I) | | | Elemental analysis (%) Found/(Calculated) | | | | | NMR (δ CCl₄/TMS) 100 MHz | | |
|---|---|---|---|---|---|---|---|---|---|---|---|
| | $X_1$ | $X_2$ | $X_3$ | C | H | Cl | F | N | a | b | C* |
| (1) | Cl | Cl | H | 51.68 | 3.44 | 19.30 | — | 3.79 | 4.92 | 3.92 | 2.16 |
| | | | | (51.89) | (3.51) | (19.19) | — | (3.78) | (1H, m) | (4H, m) | (2H, m) |
| (2) | Cl | Cl | F | 49.21 | 2.68 | 18.10 | 4.94 | 3.70 | 4.90 | 3.90 | 2.20 |
| | | | | (49.61) | (2.84) | (18.35) | (4.91) | (3.62) | (1H, m) | (4H, m) | (2H, m) |
| (3) | H | CF₃ | H | 55.41 | 3.84 | — | 15.38 | 3.64 | 4.95 | 4.00 | 2.22 |
| | | | | (55.28) | (3.79) | — | (15.45) | (3.79) | (1H, m) | (4H, m) | (2H, m) |
| (4) | Cl | CF₃ | H | 50.41 | 3.12 | 8.92 | 14.15 | 3.50 | 4.94 | 3.86 | 2.16 |
| | | | | (50.56) | (3.22) | (8.80) | (14.13) | (3.47) | (1H, m) | (4H, m) | (2H, m) |

TABLE 1-continued

| Compound No. | Substituents in formula (I) | | | Elemental analysis (%) Found/(Calculated) | | | | | NMR ($\delta_{TMS}^{CCl_3}$) 100 MHz | | |
|---|---|---|---|---|---|---|---|---|---|---|---|
| | $X_1$ | $X_2$ | $X_3$ | C | H | Cl | F | N | a | b | C* |
| (5) | Cl | Cl | Cl | 47.51 (47.47 | 2.99 2.97 | 26.21 26.33 | — — | 3.42 3.46 | 4.90 (1H, m) | 3.90 (4H, m) | 2.20 (2H, m) |

Note *

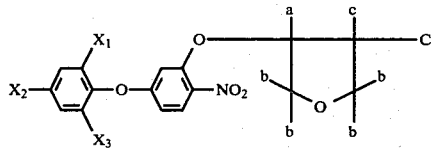

It has been known that some kinds of diphenyl ether compounds have superior herbicidal characteristics. For example, 2,4-dichlorophenyl-3-methoxy-4-nitrophenyl ether (to be abbreviated chlormethoxynil) has been used widely as a herbicide for the early stage of cultivation in rice paddies. It has been desired however to develop herbicides having higher selectivity for rice and herbicidal action against weeds, and for this purpose, a number of diphenyl ether compounds have been investigated for their practical applicability. Since these compounds differ markedly in the presence or absence and the degree of herbicidal activity, the mode of exhibiting herbicidal activity, selectivity and residual efficacy depending upon differences in chemical structure, for example in the types, numbers or positions of substituents, it is extremely difficult to anticipate the activities of these compounds by analogy from the chemical structures of known diphenyl ether compounds.

It is an object of this invention therefore to provide a novel herbicide having excellent practical utility by producing it commercially advantageously.

We have synthesized various novel diphenyl ether compounds and evaluated their herbicidal activities. Consequently, we have discovered that diphenyl ether compounds as novel tetrahydrofuran derivatives of general formula (I) have better herbicidal activity and higher selectivity than that of chlormethoxynil.

A group of compounds of general formula (I) as an active ingredient of the herbicide of this invention exhibit various superior herbicidal characteristics in comparison with chlormethoxynil. For example, these compounds have higher activity at low concentrations against many weeds in paddy fields including barnyard grass (*Echinochloa crusgalli*) which is a very hazardous weed in a paddy field, and extremely low phytotoxicity on aquatic rice plants as compared with chlormethoxynil. In upland farms, these compounds have high activity at low concentrations against crabgrass (*Digitaria sanguinalis*) and foxtail (*Setaria viridis*) which are very hazardous weeds and other upland weeds with very low phytotoxicity on soybean and other useful crops as compared with 2,4-dichlorophenyl-4-nitrophenyl ether (to be abbreviated NIP).

The compound of formula (I) of this invention can be used, or formulated, in admixture with other herbicides, insecticides, fungicides, plant growth regulators, soil conditioners, or fertilizable substances. Examples of the other herbicides which may be used together with the herbicide of this invention include the following.

Triazine-type herbicides

2-Chloro-4,6-bis(ethylamino)-1,3,5-triazine,
2,4-bis(ethylamino)-6-methylthio-1,3,5-triazine,
2-chloro-4-ethylamino-6-isopropylamino-1,3,5-triazine,
2-ethylamino-4-isopropylamino-6-methylthio-1,3,5-triazine, and
2-chloro-4-diethylamino-6-ethylamino-1,3,5-triazine.

Urea-type herbicides 3-(3,4-Dichlorophenyl)-1,1-dimethylurea,
3-(3,4-dichlorophenyl)-1-methoxy-1-methylurea,
1,1-dimethyl-3-(3-trifluoromethylphenyl)urea,
1-(2-methylcyclohexyl)-3-phenylurea,
3-(4-chlorophenyl)-1-methoxy-1-methylurea,
3-[4-(4-chlorophenoxy)phenyl]-1,1-dimethylurea, and
3-[4-(4-methoxyphenoxy)phenyl]-1,1-dimethylurea.

Acid anilide-type herbicides

3',4'-Dichloropropionanilide,
2-methyl-4-chlorophenoxyaceto-O-chloroanilide,
5-chloro-4-methyl-2-propionanilide-1,3-thiazole,
2-chloro-(2',6'-dinitroanilino)-N-methylpropionamide,
2-chloro-2',6'-diethyl-N-(butoxymethyl)acetanilide,
2-chloro-2',6'-diethyl-N-(propoxyethyl)acetanilide, and
2-chloro-N-isopropylacetanilide.

Hydroxybenzonitrile-type herbicides

4-Hydroxy-3,5-diiodobenzonitrile,
3,5-dibromo-4-hydroxybenzonitrile, and
4-hydroxy-3,5-diiodobenzonitrile octanoate.

Uracil-type herbicides 3-tert-Butyl-5-chloro-6-methyluracil,
5-bromo-3-sec-butyl-6-methyluracil, and
3-cyclohexyl-5,6-trimethyleneuracil.

Diphenylether-type herbicides 2,4-Dichloro-4'-nitrodiphenyl ether,
2,4,6-trichloro-4'-nitrodiphenyl ether,
2,4-dichloro-3'-methoxy-4'-nitrodiphenyl ether,
2-nitro-4-trifluoromethyl-4'-nitrodiphenyl ether,
2-chloro-4-trifluoromethyl-4'-nitrodiphenyl ether,
2-chloro-4-trifluoromethyl-3'-methoxycarbonyl-4'-nitrodiphenyl ether, and
methyl-2-[4-(2,4-dichlorophenoxy)phenoxy]propionate.

Carbamate-type herbicides

Isopropyl-N-phenyl carbamate,
isopropyl-N-(3-chlorophenyl)carbamate.
methyl-N-(3,4-dichlorophenyl)carbamate,
S-ethyldipropyl thiocarbamate,
S-p-chlorobenzyldiethyl thiocarbamate,
methyl-N-(4-amino-benzenesulfonyl)carbamate,
ethyl-N,N-di-n-propylthiol carbamate,
4-chlorobenzyl-N,N-diethyl thiocarbamate, and ethyl-N,N-hexamethylenethiol carbamate.

Aniline-type herbicides 2,6-Dinitro-N,N-dipropyl-4-trifluoromethylaniline,
N-butyl-N-ethyl-2,6-dinitro-4-trifluoromethylaniline, and
3,4-dimethyl-2,6-dinitro-N-1-ethylpropylaniline.

Pyridinium salt-type herbicides 1,1'-Dimethyl-4,4'-bispyridinium dichloride, and
9,10-dihydroxy-8a,10a-diazoniaphenanthrone dibromide.

Other herbicides

N,N-bis(phosphonomethyl)glycine,
α,α,α-trifluoro-2,6-dinitro-N,N-dipropyl-p-toluidine,
S-(2-methyl-1-piperidylcarbonylmethyl)-O,O-dipropylphosphorodithioate,
4-amino-6-tert-butyl-3-methylthio-1,2,4-triazin-5(4H)-one,
O-ethyl-O-(2-nitro-5-methylphenyl)-N-sec-butylphosphoroamidothioate,
N-(O,O-dipropyldithiophosphorylacetyl)-2-methylpiperidine, and
2,4-diamino-5-methylthio-6-chloropyrimidine.

The amount of the compound of formula (I) in the herbicide of this invention is desirably 2 to 10% for granules, 20 to 80% for wettable powders, and 10 to 50% for emulsifiable concentrates.

The following Examples illustrate the formulation of the herbicide of this invention, but the present invention is not limited thereto. All parts in these Examples are by weight. The compound numbers in these examples correspond to those shown in Table 1.

EXAMPLE 1

(granules)

Six parts of compound No. (1), 70 parts of bentonite, 21 parts of talc, 2 parts of sodium dodecylbenzenesulfonate and 1 part of sodium ligninsulfonate were mixed, and kneaded together with a suitable amount of water. The mixture was granulated in a customary manner by an extruding granulator, and dried to afford 100 parts of granules.

EXAMPLE 2

(wettable powder)

Twenty parts of compound No. (2), 70 parts of diatomaceous earth and 10 parts of sodium dodecylbenzenesulfonate were mixed and pulverized to obtain 100 parts of a wettable powder.

EXAMPLE 3

(emulsifiable concentrate)

Ten parts of compound No. (1), 10 parts of Sorpol (a trademark for an emulsifier manufactured by Toho Chemical Co., Ltd), and 80 parts of benzene were mixed to obtain 100 parts of an emulsifiable concentrate.

The following Test Examples specifically illustrate the excellent herbicidal effect and selectivity of the compounds of this invention. The compound numbers in these examples correspond to those shown in Table 1.

Test Example 1

Herbicidal test for paddy field:

A Wagner pot (a/5000) was filled with soil, and seeds of *Echinochloa crusgalli, Scirpus juncoides, Alisma canaliculatum,* or *Cyperus difformis* were sown. The pot was then irrigated. Two groups of rice seedlings (three-leaf stage) each consisting of two seedlings, which had been grown in advance, were transplanted into the pot, and grown in a greenhouse. Three days after transplantation of rice seedlings when weeds began to occur, granules containing a predetermined amount of each of test compounds prepared by the method described in Example 1 were applied to the irrigated soil in the pot. One month after this treatment, the state of weed occurrence and phytotoxicity on rice plants were examined, and the results are shown in Table 2. The degree of phytotoxicity on the crop (rice) and the herbicidal efficacy against the weeds were determined by calculating the percentage of the dry weight of surviving rice plants or weeds based on that of rice plants or weeds in an untreated lot, and evaluating it on a scale of 0 to 5 as shown below (the same method was used in the subsequent Test Examples).

| Standards of evaluation | |
| --- | --- |
| 0: | 91–100% |
| 1: | 61–90% |
| 2: | 31–60% |
| 3: | 11–30% |
| 4: | 6–10% |
| 5: | 0–5% |

TABLE 2

| Tested compound No. | Amount of the active ingredient (g/a) | Echinochloa crusgalli | Scirpus juncoides | Alisma canaliculatum | Cyperus difformis | Rice |
| --- | --- | --- | --- | --- | --- | --- |
| (1) | 1 | 5 | 4 | 5 | 5 | 0 |
|  | 2 | 5 | 5 | 5 | 5 | 0 |
|  | 5 | 5 | 5 | 5 | 5 | 0 |
| (2) | 1 | 5 | 5 | 5 | 5 | 0 |
|  | 2 | 5 | 5 | 5 | 5 | 0 |
|  | 5 | 5 | 5 | 5 | 5 | 0 |
| (3) | 1 | 5 | 4 | 5 | 5 | 0 |
|  | 2 | 5 | 5 | 5 | 5 | 0 |
|  | 5 | 5 | 5 | 5 | 5 | 0 |
| (4) | 1 | 5 | 5 | 5 | 5 | 0 |
|  | 2 | 5 | 5 | 5 | 5 | 0 |
|  | 5 | 5 | 5 | 5 | 5 | 0 |
| Control (Chlormethoxynil) | 5 | 3 | 3 | 5 | 4 | 0 |
|  | 10 | 4 | 4 | 5 | 5 | 0 |
|  | 20 | 5 | 5 | 5 | 5 | 1 |

Test Example 2

Paddy weed control test:

A Wagner pot (a/5000) was filled with soil, and seeds of *Echinochloa crusgalli, Scirpus juncoides, Alisma canaliculatum*, or *Cyperus difformis* were sown. The pot was then irrigated. Two grams of rice seedlings (three-leaf stage) each consisting of two seedlings, which had been grown in advance, were transplanted into the pot, and grown in a green house. Ten days after transplantation of rice seedlings when weeds were growing, granules containing a predetermined amount of each of test compounds prepared by the method described in Example 1 were applied to the irrigated soil in the pot. One month after this treatment, the state of weed occurrence and phytotoxicity on rice plants were examined, and the results are shown in Table 3.

TABLE 3

| Tested compound No. | Amount of the active ingredient (g/a) | Echinochloa crusgalli | Scirpus juncoides | Alisma canaliculatum | Cyperus difformis | Rice |
|---|---|---|---|---|---|---|
| (1) | 2 | 5 | 4 | 5 | 5 | 0 |
|  | 5 | 5 | 5 | 5 | 5 | 0 |
|  | 10 | 5 | 5 | 5 | 5 | 0 |
| (2) | 2 | 5 | 5 | 5 | 5 | 0 |
|  | 5 | 5 | 5 | 5 | 5 | 0 |
|  | 10 | 5 | 5 | 5 | 5 | 0 |
| (3) | 2 | 5 | 5 | 5 | 5 | 0 |
|  | 5 | 5 | 5 | 5 | 5 | 0 |
|  | 10 | 5 | 5 | 5 | 5 | 0 |
| (4) | 2 | 5 | 5 | 5 | 5 | 0 |
|  | 5 | 5 | 5 | 5 | 5 | 0 |
|  | 10 | 5 | 5 | 5 | 5 | 0 |
| (5) | 2 | 5 | 4 | 5 | 5 | 0 |
|  | 5 | 5 | 4 | 5 | 5 | 0 |
|  | 10 | 5 | 5 | 5 | 5 | 0 |
| Control (Chlormethoxynil) | 10 | 4 | 2 | 4 | 4 | 0 |
|  | 20 | 5 | 3 | 5 | 5 | 1 |
|  | 50 | 5 | 3 | 5 | 5 | 1 |

Test Example 3

Upland farm weed control test:

A wagner pot (a/5000) was filled with soil, and seeds of soybeans, cotton or corn and *Digitaria sanguinalis, Setaria viridis, Amaranthus retroflexus,* or *Chenopodium album* were sown. Three days after sowing, a predetermined amount of a wettable powder containing each of the test compounds, which had been prepared in accordance with the method of Example 2, was diluted with 10 liters, per are, of water, and sprayed by means of a slight pressure sprayer.

These plants were grown in a greenhouse. Thirty days after the spraying of the herbicide, the state of weed occurrence and the state of growth of the plant was examined, and the results shown in Table 4 were obtained.

TABLE 4

| Tested compound No. | Amount of the active ingredient (g/a) | Digitaria sanguinalis | Setaria viridis | Amaranthus retroflexus | Chenopodium album | Soybean | Cotton | Corn |
|---|---|---|---|---|---|---|---|---|
| (1) | 5 | 5 | 4 | 5 | 5 | 0 | 0 | 0 |
|  | 10 | 5 | 5 | 5 | 5 | 0 | 0 | 0 |
|  | 20 | 5 | 5 | 5 | 5 | 0 | 1 | 0 |
| (2) | 5 | 5 | 5 | 5 | 5 | 0 | 0 | 0 |
|  | 10 | 5 | 5 | 5 | 5 | 0 | 0 | 0 |
|  | 20 | 5 | 5 | 5 | 5 | 0 | 0 | 0 |
| (3) | 5 | 5 | 4 | 5 | 5 | 0 | 0 | 0 |
|  | 10 | 5 | 5 | 5 | 5 | 0 | 0 | 0 |
|  | 20 | 5 | 5 | 5 | 5 | 0 | 0 | 0 |
| (4) | 5 | 5 | 5 | 5 | 5 | 0 | 0 | 0 |
|  | 10 | 5 | 5 | 5 | 5 | 0 | 0 | 0 |
|  | 20 | 5 | 5 | 5 | 5 | 0 | 0 | 0 |
| (5) | 5 | 4 | 4 | 5 | 5 | 0 | 0 | 0 |
|  | 10 | 5 | 5 | 5 | 5 | 0 | 0 | 0 |
|  | 20 | 5 | 5 | 5 | 5 | 0 | 0 | 0 |
| Control (NIP) | 10 | 3 | 3 | 4 | 3 | 0 | 0 | 0 |
|  | 20 | 4 | 4 | 5 | 4 | 0 | 0 | 0 |
|  | 50 | 4 | 4 | 5 | 5 | 1 | 0 | 0 |

Test Example 4

Upland farm weed control test:

A pot (a/1000) was filled with soil, and seeds of wheat, corn, soybean, cotton or beet, and *Setaria viridis, Echinochloa crusgalli, Sorghum halepense, Amaranthus retroflexus, Chenopodium album, Brassica kaber, Polygonum nodosum, Xanthium strumarium, Ipomoea lacunosa, Lanium purpureum* or *Stellaria media* were sown. They were grown in a greenhouse. When those plants grew to a 2- to 3-leaf stage, a predetermined amount of an emulsifiable concentrate containing each of the test compounds which had been prepared by the method of Example 3, was diluted with 10 liters, per are, of water, and sprayed by means of a slight pressure sprayer.

Thirty days after the treatment, the state of growth of the crop and the weeds were examined, and the results shown in Table 5 were obtained.

TABLE 5

| Tested compound No. | (1) | | | (2) | | | (3) | | | (4) | | | (5) | | | Blazer (*) | | |
|---|---|---|---|---|---|---|---|---|---|---|---|---|---|---|---|---|---|---|
| Amount of the active ingredient (g/a) | 5 | 10 | 20 | 5 | 10 | 20 | 5 | 10 | 20 | 5 | 10 | 20 | 5 | 10 | 20 | 5 | 10 | 20 |
| Digitaria sanguinalis | 3 | 4 | 5 | 3 | 4 | 5 | 3 | 3 | 4 | 4 | 5 | 5 | 3 | 4 | 4 | 4 | 5 | 5 |
| Setaria viridis | 3 | 3 | 5 | 3 | 4 | 5 | 4 | 5 | 5 | 5 | 5 | 5 | 4 | 5 | 5 | 3 | 4 | 5 |
| Echinochloa crusgalli | 3 | 4 | 4 | 4 | 4 | 4 | 3 | 3 | 4 | 5 | 5 | 5 | 3 | 4 | 5 | 1 | 2 | 3 |
| Sorghum halepense | 2 | 2 | 3 | 3 | 3 | 3 | 1 | 2 | 3 | 2 | 3 | 4 | 1 | 2 | 3 | 3 | 4 | 5 |
| Amaranthus retroflexus | 5 | 5 | 5 | 5 | 5 | 5 | 5 | 5 | 5 | 5 | 5 | 5 | 5 | 5 | 5 | 5 | 5 | 5 |
| Chenopodium album | 5 | 5 | 5 | 5 | 5 | 5 | 5 | 5 | 5 | 5 | 5 | 5 | 5 | 5 | 5 | 5 | 5 | 5 |
| Brassica kaber | 4 | 5 | 5 | 5 | 5 | 5 | 3 | 4 | 5 | 5 | 5 | 5 | 4 | 5 | 5 | 5 | 5 | 5 |
| Polygonum nodosum | 5 | 5 | 5 | 5 | 5 | 5 | 5 | 5 | 5 | 5 | 5 | 5 | 5 | 5 | 5 | 5 | 5 | 5 |
| Lanium purpureum | 5 | 5 | 5 | 5 | 5 | 5 | 5 | 5 | 5 | 5 | 5 | 5 | 5 | 5 | 5 | 5 | 5 | 5 |
| Ipomoea lacunosa | 5 | 5 | 5 | 5 | 5 | 5 | 5 | 5 | 5 | 5 | 5 | 5 | 5 | 5 | 5 | 5 | 5 | 5 |
| Xanthium strumarium | 5 | 5 | 5 | 5 | 5 | 5 | 5 | 5 | 5 | 5 | 5 | 5 | 5 | 5 | 5 | 5 | 5 | 5 |
| Stellaria media | 4 | 5 | 5 | 4 | 5 | 5 | 4 | 4 | 4 | 5 | 5 | 5 | 4 | 5 | 5 | 5 | 5 | 5 |
| Wheat | 1 | 1 | 1 | 1 | 1 | 1 | 1 | 1 | 1 | 1 | 2 | 2 | 1 | 1 | 1 | 2 | 2 | 2 |
| Corn | 0 | 1 | 1 | 0 | 1 | 1 | 0 | 1 | 1 | 1 | 1 | 1 | 1 | 1 | 1 | 2 | 2 | 3 |
| Soybean | 1 | 1 | 1 | 1 | 1 | 2 | 0 | 1 | 1 | 1 | 2 | 2 | 0 | 0 | 1 | 0 | 0 | 1 |
| Cotton | 1 | 1 | 1 | 1 | 1 | 1 | 1 | 1 | 1 | 1 | 1 | 2 | 1 | 1 | 1 | 4 | 4 | 4 |
| Beet | 1 | 1 | 1 | 1 | 1 | 2 | 1 | 1 | 1 | 2 | 2 | 2 | 1 | 1 | 2 | 2 | 5 | 8 |

(*) 2-Chloro-4-trifluoromethyl-3'-carboxylic acid 4'-nitrodiphenyl ether.

What we claim is:

1. A tetrahydrofuran derivative represented by the general formula

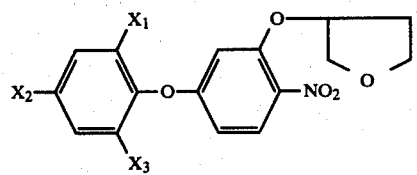

wherein $X_1$ and $X_3$ represent a hydrogen or halogen atom, and $X_2$ represents a halogen atom or a trifluoromethyl group.

2. The compound of claim 1 wherein $X_1$ and $X_2$ are chlorine atoms, and $X_3$ is a hydrogen or chlorine atom.

3. The compound of claim 1 wherein $X_1$ and $X_3$ are hydrogen atoms, and $X_2$ is a trifluoromethyl group.

4. The compound of claim 1 wherein $X_1$ is a chlorine atom, $X_2$ is a trifluoromethyl group, and $X_3$ is a hydrogen atom.

5. A herbicidal composition comprising as an active ingredient a herbicidally effective amount of a tetrahydrofuran derivative of the formula

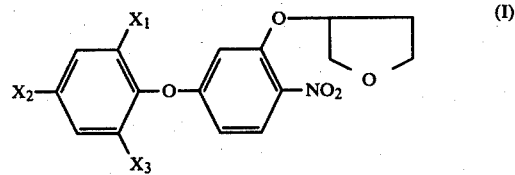

wherein $X_1$ and $X_3$ represent a hydrogen or halogen atom, and $X_2$ represents a halogen atom or a trifluoromethyl group and an inert carrier or vehicle.

6. The composition of claim 5 wherein $X_1$ and $X_2$ are chlorine atoms, and $X_3$ is a hydrogen or chlorine atom.

7. The composition of claim 5 wherein $X_1$ and $X_3$ are hydrogen atoms, and $X_2$ is a trifluoromethyl group.

8. The composition of claim 5 wherein $X_1$ is a chlorine atom, $X_2$ is a trifluoromethyl group, and $X_3$ is a hydrogen atom.

* * * * *